United States Patent [19]

Ascione et al.

[11] Patent Number: 5,672,337
[45] Date of Patent: Sep. 30, 1997

[54] AMIDO PHOTOSTABILIZATION OF DIBENZOYLMETHANE SUNSCREENS

[75] Inventors: Jean-Marc Ascione, Paris; Serge Forestier, Claye Souilly; Pascal Sterle, Soisy/Montmorency, all of France

[73] Assignee: L'Oreal, Paris, France

[21] Appl. No.: 571,340

[22] Filed: Dec. 12, 1995

[30] Foreign Application Priority Data

Dec. 12, 1994 [FR] France ................. 94 14930

[51] Int. Cl.$^6$ ................. A61K 7/42; A61K 7/40
[52] U.S. Cl. ................. 424/59; 424/60; 424/400; 424/401
[58] Field of Search ................. 424/59, 60, 400, 424/401

[56] References Cited

U.S. PATENT DOCUMENTS 4,810,489  3/1989  Murray et al. ................. 424/59

FOREIGN PATENT DOCUMENTS

| 0396422 | 5/1990 | European Pat. Off. . |
| 0521651 | 6/1992 | European Pat. Off. . |
| 0604249 | 11/1993 | European Pat. Off. . |
| 2440933 | 11/1979 | France . |
| WO94/04131 | 3/1994 | WIPO . |
| WO94/14410 | 7/1994 | WIPO . |

*Primary Examiner*—Shelly A. Dodson
*Attorney, Agent, or Firm*—Burns, Doane, Swecker & Mathis, L.L.P.

[57] ABSTRACT

Topically applicable photostable sunscreen/cosmetic compositions well suited for the stable photoprotection of human skin and/or hair against the damaging effects of UV-irradiation, particularly solar radiation, comprise a photoprotecting effective amount of at least one dibenzoylmethane compound and an effective amount of at least one amido compound photostabilizer therefor, in a cosmetically acceptable vehicle, diluent or carrier.

34 Claims, No Drawings

AMIDO PHOTOSTABILIZATION OF DIBENZOYLMETHANE SUNSCREENS

BACKGROUND OF THE INVENTION

1. Technical Field of the Invention

The present invention relates to novel cosmetic compositions for topical application, for the photoprotection of the skin and/or hair against ultraviolet radiation (such compositions hereinafter simply designated "sunscreen," "sunscreen/cosmetic" or "photoprotective/sunscreen" compositions), and to the use of same for the cosmetic applications indicated above.

This invention especially relates to the light stabilization of specific, UV-A-active sunscreen agents by means of at least one amido compound and, more especially, relates to UV-stable sunscreen/cosmetic compositions which comprise, in a cosmetically acceptable vehicle, carrier or diluent, at least one dibenzoylmethane compound as a UV-A-active organic sunscreen agent, in combinatory immixture with at least one amide compound photostabilizer.

2. Description of the Prior Art

It is known to this art that UV-A radiation, of wavelengths from 320 and 400 nm, which tans the skin, also adversely affects it over time, in particular in the event of sensitive skin or a skin which is continually exposed to solar radiation.

UV-A rays cause, in particular, a loss in the elasticity of the skin and the appearance of wrinkles, promoting a premature aging thereof. Such irradiation also promotes the initiation of the erythemal reaction or accentuates this reaction in certain individuals, and may even be the source of phototoxic or photoallergic reactions. Thus, it is therefore desirable to screen out UV-A radiation.

A wide variety of organic sunscreen agents which absorb, more or less selectively, harmful or damaging UV-A irradiation are known to this art.

In this regard, a particularly attractive class of UV-A sunscreens comprises derivatives of dibenzoylmethane, and, in particular, 4-(tert-butyl)-4'-methoxydibenzoylmethane, which indeed exhibit a high intrinsic absorption capacity. These dibenzoylmethane derivatives, which are compounds per se well known to this art as UV-A-active sunscreen agents, are particularly described in FR-A-2,326,405 and FR-A-2,440,933, and in EP-A-0,114,607; 4-(tert-butyl)-4'-methoxydibenzoylmethane, moreover, is currently commercially available under the trademark "PARSOL 1789" marketed by GIVAUDAN.

Unfortunately, it has been determined that dibenzoylmethane derivatives are compounds which are relatively sensitive to ultraviolet radiation (especially UV-A); in other words, more precisely, they exhibit an unfortunate tendency to undergo more or less rapid degradation under the influence of this radiation. Therefore, this substantial lack of photochemical stability of dibenzoylmethane compounds in the face of the ultraviolet radiation to which they are, by their very nature, subjected does not permit ensuring constant protection over prolonged exposure to the sun, such that repeated applications at regular and frequent intervals must be carried out by the user to provide effective protection of the skin against UV-irradiation.

The light stabilization of dibenzoylmethane compounds vis-a-vis UV radiation continues to be a problem which has not as yet been resolved completely satisfactorily.

SUMMARY OF THE INVENTION

It has now unexpectedly and surprisingly been determined that, by intimately admixing the dibenzoylmethane compounds indicated above with an effective amount of at least one amide compound, the photochemical stability (or photostability) of these dibenzoylmethane compounds is conspicuously and substantially enhanced.

It too should be appreciated that the subject dibenzoylmethane compounds comprise lipophilic sunscreens exhibiting the property, which is also a disadvantage, of being solid at room temperature. Because of this, incorporating same into cosmetic sunscreen compositions entails certain constraints with regard to their formulation and use thereof, especially in respect of solvents which properly solubilize these compounds, whether alone or in combination with other sunscreen agents. In this regard, to date oils are frequently employed, such as esters, and more particularly $C_{12}$–$C_{15}$ alkyl benzoates ("FINSOLV TN" marketed by Finetex), or of triglycerides, and in particular $C_8$–$C_{12}$ fatty acid triglycerides ("MIGLYOL 812" marketed by Hüls), but these various products have solubilizing properties vis-a-vis the aforesaid sunscreen agents which remain inadequate.

Nonetheless, it has also been found, and this is one of the additional advantages presented by the present invention, that certain of the amide compound light stabilizers according to the present invention also comprise likewise surprisingly and unexpectedly, particularly useful solvents for the sunscreen agents of the dibenzoylmethane derivative type, such as, for example, 4-(tert-butyl)-4'-methoxydibenzoylmethane, these compounds indeed having extremely high solubilities in the subject amide compounds, and these solubilities being in any event markedly superior than those obtained with all of the other usual solvents which to date have been employed in this art, thereby making it possible, with an equal amount of solvent, to utilize greater amounts of sunscreens.

Thus, the present invention also features a technique for the stabilization of dibenzoylmethane compounds with respect to UV radiation (wavelengths of from 280 nm to 400 nm, approximately), in particular solar radiation, entailing combining such dibenzoylmethane compounds with an effective stabilizing amount of at least one amide compound.

According to the present invention, novel light-stable cosmetic sunscreen compositions are provided, for the protection of the skin and/or hair against ultraviolet radiation, especially solar radiation, comprising, in a cosmetically acceptable vehicle, diluent or carrier, at least one dibenzoylmethane compound and an effective photostabilizing amount of at least one amide compound.

The present invention also features an improved cosmetic treatment for protecting the skin and/or hair against ultraviolet radiation, especially solar radiation, which comprises topically applying to the skin and/or hair an effective amount of a light-stable composition as described above.

Lastly, the present invention features the use of an amide compound for stabilizing, with respect to UV irradiation, a dibenzoylmethane compound which comprises a cosmetic sunscreen composition.

DETAILED DESCRIPTION OF BEST MODE AND SPECIFIC/PREFERRED EMBODIMENTS OF THE INVENTION

More particularly according to the present invention, the dibenzoylmethane compounds thus stabilized are per se well known to this art and are described, in particular, in FR-A-2,326,405, FR-A-2,440,933 and EP-A-0,114,607 indicated above, hereby expressly incorporated by reference.

It will of course be appreciated that one or more such dibenzoylmethane compounds can thus be employed.

Exemplary dibenzoylmethane compounds which are thus representative include:

2-Methyldibenzoylmethane,
4-Methyldibenzoylmethane,
4-Isopropyldibenzoylmethane,
4-Tert-butyldibenzoylmethane,
2,4-Dimethyldibenzoylmethane,
2,5-Dimethyldibenzoylmethane,
4,4'-Diisopropyldibenzoylmethane,
4-Tert-butyl-4'-methoxydibenzoylmethane,
2-Methyl-5-isopropyl-4'-methoxydibenzoylmethane,
2-Methyl-5-tert-butyl-4'-methoxydibenzoylmethane,
2,4-Dimethyl-4'-methoxydibenzoylmethane,
2,6-Dimethyl-4-tert-butyl-4'-methoxydibenzoylmethane.

Among the aforesaid dibenzoylmethane compounds, particularly preferred is 4-(tert-butyl)-4'-methoxydibenzoylmethane, especially that marketed under the trademark "PARSOL 1789" by GIVAUDAN, this sunscreen having the structural formula:

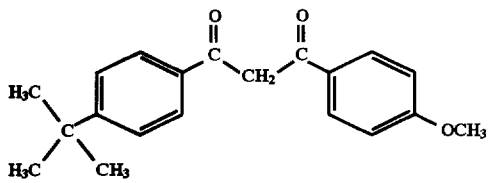

Another preferred dibenzoylmethane compound in accordance with the present invention is 4-isopropyldibenzoylmethane, a sunscreen agent which is marketed under the trademark "EUSOLEX 8020" by MERCK, having the structural formula:

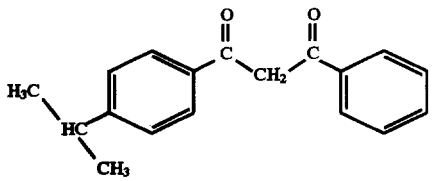

The dibenzoylmethane compound or compounds are advantageously present in the compositions of the invention, or in compositions which are stabilized in accordance therewith, in amounts generally ranging from 0.01% to 10% by weight, preferably from 0.1% to 6% by weight, relative to the total weight of the composition.

Per the present invention, by the term "amide compound" is intended any compound which in its chemical structure has at least one amide group (or amide function):

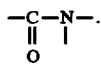

By the term "effective amount of amide compound" is intended an amount which is sufficient to elicit a marked and significant improvement in the light stability of the dibenzoylmethane compound or compounds which are present in the composition. This minimum amount of stabilizer to be employed, which may vary according to the nature of the cosmetically acceptable vehicle, diluent or carrier comprising said composition can be determined without difficulty via a conventional test for measuring light stability, such as that reported in the examples below.

In general, the amide compound or compounds can therefore be present in the compositions of the invention, or employed in the process according to the invention, in amounts which advantageously range from 0.01% to 50% by weight, preferably from 0.1% to 30% by weight, relative to the total weight of the composition.

The amide compounds which are particularly preferred according to the present invention include those of the following structural formula (1):

in which the radicals $R^1$, $R^2$ and $R^3$, which may be identical or different, are each a hydrogen atom or a monovalent, saturated or unsaturated, aliphatic, cycloaliphatic or cyclic hydrocarbon radical, optionally containing at least one functional group, and having from 1 to 30 carbon atoms, preferably 1 to 22 carbon atoms, inclusive, with the proviso that the radical $R^1$ can together form, with the radical $R^2$ or with the radical $R^3$, a ring member having from 5 to 18 carbon atoms, inclusive, and that the radicals $R^2$ and $R^3$ can together form a ring member having from 5 to 18 carbon atoms, inclusive.

Exemplary saturated aliphatic hydrocarbon radicals which are particularly representative include linear or branched, substituted or unsubstituted $C_1$–$C_{30}$, preferably $C_1$–$C_{22}$, alkyl radicals, and in particular methyl, ethyl, n-propyl, isopropyl, n-butyl, isobutyl, tert-butyl, pentyl, n-amyl, isoamyl, neopentyl, n-hexyl, n-heptyl, n-octyl, 2-ethylhexyl, tert-octyl, decyl, lauryl and octadecyl radicals.

Exemplary saturated cyclic hydrocarbon radicals which are particularly representative include cyclopentyl and cyclohexyl radicals, whether unsubstituted or substituted, in particular, by alkyl radicals.

Exemplary unsaturated aliphatic hydrocarbon radicals which are particularly representative include linear or branched, unsubstituted or substituted, $C_2$–$C_{30}$, preferably $C_2$–$C_{22}$, alkenyl or alkynyl radicals, and especially vinyl, allyl, oleyl and linoleyl radicals.

And exemplary unsaturated cyclic hydrocarbon radicals which are particularly representative are phenyl and naphthyl radicals, optionally substituted, in particular by alkyl radicals, for example the tolyl radical. Exemplary unsaturated cycloaliphatic radicals include, more particularly, the benzyl and phenylethyl radicals.

By the term "optionally containing at least one functional group" is intended a radical comprising, whether in the principal chain or on a secondary chain moiety thereof, one or more functional groups which are, in particular, of the ester, ether, alcohol, amine, amide and ketone type, but which are preferably esters.

Exemplary amide compounds of formula (1) according to the present invention, more particularly preferred are compounds which have at least one, and even more preferably all of the following characteristics:

(i) the amide compound is an N-substituted amide, and still more preferably an N,N-disubstituted amide, (ii) $R^1$ is a preferably $C_1$–$C_{22}$, and still more preferably a $C_1$–$C_{12}$, linear or branched alkyl radical, or a phenyl radical which is itself unsubstituted or substituted by one or more $C_1$–$C_{12}$ linear or branched alkyl radicals, (iii) $R^2$ is a preferably $C_1$–$C_{22}$ and, still more preferably a $C_1$–$C_{12}$ linear or branched alkyl radical, (iv) $R^3$ is a linear or branched alkyl radical $R^2$, or a monovalent radical comprising an ester functional group which corresponds to the following structural formula (2):

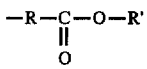 (2)

in which R and R', which may be identical or different, represent two hydrocarbon radicals, preferably alkyl radicals, having from 1 to 12 carbon atoms, preferably 1 to 8 carbon atoms.

In one embodiment of the present invention, the amide compounds, especially those described above, are those in which the dibenzoylmethane compound or compounds to be stabilized have good solubility.

In another embodiment of the present invention, the amide compounds, especially those described above, are those having a good solubility in the fatty phases which are conventionally used for the formulation of cosmetically acceptable vehicles.

In yet another embodiment of the present invention, the amide compounds, especially those described above, are employed in an amount which is alone sufficient to solubilize the dibenzoylmethane compound or compounds to be stabilized.

In another embodiment of the present invention, the amide compounds, especially those described above, are N,N-disubstituted.

In still another embodiment of the present invention, the amide compounds, especially those described above, are those which are devoid, or substantially devoid, of any emulsifying property.

And in yet another embodiment of the present invention, the amide compounds, especially those described above, are nonionic.

In another embodiment of the present invention, the amide compounds, especially those described above, are those which are insoluble in water or substantially insoluble in water.

It will of course be appreciated that each of the above embodiments may be considered alone (i.e., separately) or, in contrast, in combination, such as, for example, the event of an embodiment entailing an amide compound which simultaneously is N,N-disubstituted and has no emulsifying properties, or else the embodiment entailing an amide compound which is at the same time nonemulsifying, nonionic and insoluble in water.

Particularly representative specific amide compounds which have conspicuously remarkable properties in respect of the photochemical stabilization of dibenzylmethane derivatives include:

(a) N,N-diethyl-methylbenzamides having the formula (3):

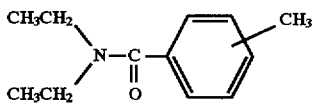 (3)

including N,N-diethyl-3-methylbenzamide (Compound 1), and (b) ethyl N-butyl-N-acetylaminopropionate (Compound 2), having the formula (4):

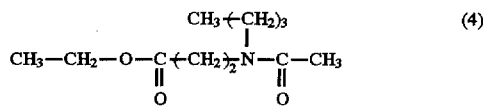 (4)

Moreover, it too has been found that these specific compounds are excellent solvents for dibenzoylmethane derivatives. Thus, for example, it has been observed that, at room temperature, the sunscreen 4-(tert-butyl)-4'-methoxydibenzoylmethane can be dissolved in an amount of approximately 40% by weight in the compounds of formula (3) and in an amount of approximately 30% by weight in compound 2. By comparison, this sunscreen can only be dissolved in an amount of approximately 20% by weight in a reference solvent such as the aforesaid FINSOLV TN.

Strictly from the standpoint of light stabilization, Compound 2 is preferred over Compound 1 in accordance with the present invention.

The photostable sunscreen/cosmetic compositions according to the invention can of course contain, in addition to the dibenzoylmethane compounds, one or more complementary UVA- and/or UVB-active, hydrophilic or lipophilic, sunscreen agents. The presence of complementary sunscreens which are active in UV-B range (at wavelengths ranging from approximately 280 nm to 320 nm) thus provides final compositions which are suitable for filtering the broad spectrum of UV irradiation.

The compositions of the invention may additionally comprise conventional cosmetic adjuvants and additives selected, in particular, from among fats, organic solvents, ionic or nonionic thickeners, demulcents, antioxidants, opacifying agents, stabilizers, emollients, silicones, α-hydroxy acids, antifoams, moisturizers, vitamins, fragrances, preservatives, surfactants, fillers, insect repellants, pigments (inorganic or organic), sequestrants, polymers, propellants, basifying or acidifying agents, dyes, colorants, or any other ingredient which is typically employed in cosmetics, especially for the production of sunscreen/cosmetic compositions in emulsion form. All of the supplementary ingredients which can be introduced into the compositions of the invention of course must not interfere with or exert any substantial adverse affect on the light stabilization elicited by the amide compounds on the dibenzoylmethanes.

The fats may comprise an oil or a wax or mixtures thereof, and may also comprise fatty acids, fatty alcohols and fatty acid esters. The oils are advantageously selected from among animal oils, vegetable oils, mineral oils or synthetic oils, and in particular from among liquid petroleum, paraffin oil, silicone oils, whether volatile or nonvolatile, isoparaffins, poly-α-olefins, fluorinated oils and perfluorinated oils. Similarly, the waxes are advantageously selected from among animal waxes, fossil waxes, vegetable waxes, mineral waxes or synthetic waxes which are per se known to this art.

Exemplary organic solvents include the alcohols and lower polyols.

The thickeners are advantageously selected, in particular from among crosslinked polyacrylic acids, guar gums and celluloses, modified or otherwise, such as hydroxypropylated guar gum, methylhydroxyethylcellulose, hydroxypropylmethylcellulose and hydroxyethylcellulose.

The compositions of the invention can be formulated according to techniques well known to this art, especially those intended for the preparation of oil-in-water or water-in-oil emulsions.

The subject compositions may, in particular, be in the form of a simple or complex emulsion (O/W, W/O, O/W/O or W/O/W) such as a cream, milk, gel or cream gel, ointment, lotion, powder, solid stick, and may be packaged as an aerosol and be provided in the form of a foam or spray.

When it is an emulsion, the aqueous phase of this emulsion may comprise a nonionic vesicle dispersion which is prepared according to known processes (Bangham, Standish and Watkins, *J. Mol. Biol.*, 13, 238 (1965), FR-2,315,991 and FR-2,416,008).

The photostable sunscreen/cosmetic compositions of the invention are useful for protecting the human skin (epidermis) or hair against the damaging effects of ultraviolet radiation, as sunscreen compositions or else as makeup products.

When the cosmetic compositions according to the invention are used for the photoprotection of the human skin against UV rays, or as sunscreen compositions, they may be formulated as a suspension or dispersion in solvents or in the form of a nonionic vesicle dispersion or else in the form of an emulsion, preferably of the oil-in-water type, such as a cream or milk, as in the form of an ointment, lotion, pomade, gel, cream gel, solid stick, aerosol foam or spray.

When the cosmetic compositions according to the invention are used for the photoprotection of the hair, they may be formulated as a shampoo, lotion, gel, emulsion, nonionic vesicle dispersion, or hair lacquer and may constitute, for example, a rinsing composition for application before or after shampooing, before or after dyeing or bleaching, before, during or after permanent-waving, or hair straightening, as a styling or treatment lotion or gel, as a blow-drying or hair-setting lotion or gel, as a permanent-wave composition or hair-straightening composition, or as a composition for dyeing or bleaching the hair.

When the subject compositions are used as makeup products for the eyelashes, eyebrows or skin, such as a skin treatment cream, foundation, lipstick, eyeshadow, blush, mascara, or eyeliner, they may be in solid or paste form, anhydrous or aqueous, as oil-in-water or water-in-oil emulsions, nonionic vesicle dispersions or suspensions.

The cosmetic treatment of the skin or hair to protect same against the deleterious effects of UV irradiation, comprises applying to the skin or hair an effective amount of a photostable sunscreen/cosmetic composition as described above.

In order to further illustrate the present invention and the advantages thereof, the following specific examples are given, it being understood that same are intended only as illustrative and in nowise limitative.

EXAMPLE 1

In this example, the light stability of 4-(tert-butyl)-4'-methoxydibenzoylmethane (sunscreen "PARSOL 1789" marketed by GIVAUDAN) was investigated in the presence of two amide compounds in accordance with the invention, namely, N,N-diethyl-3-methylbenzamide (Compound 1) and ethyl N-butyl, N-acetylaminopropionate (Compound 2), both of which are also solvents for this sunscreen agent. By way of comparison, the photostability of the same sunscreen agent was investigated in the absence of any amide compound, in which case the solvent used, which was neutral with respect to the sunscreen agent studied, was FINSOLV TN marketed by FINETEX ($C_{12}$–$C_{15}$ alkyl benzoates). The compositions of these three formulae (F0-F1-F2) were thus as follows (in% by weight relative to the total weight of the composition):

TABLE 1

| | Compositions (% by weight) | | |
|---|---|---|---|
| F0 (Comparative) | PARSOL 1789: 2% | FINSOLV TN: 10% | Common vehicle* |
| F1 (Invention) | PARSOL 1789: 2% | Composition 1: 10% | Common vehicle* |
| F2 (Invention) | PARSOL 1789: 2% | Composition 2: 10% | Common vehicle* |

*the composition of the common vehicle itself was as follows (in % by weight relative to the total weight of the composition):

| | |
|---|---|
| (a) Emulsifier ("SIMULSOL 165" marketed by SEPPIC) | 2% |
| (b) Thickener ("PEMULEN TR1" marketed by GOODRICH) | 0.5% |
| (c) Moisturizers (sorbitol and glycerin) | 5% |
| (d) Sequestrant (EDTA, disodium salt) | 0.1% |
| (e) pH regulator (triethanolamine) | 0.5% |
| (f) Distilled water qs | 100% |

The light stability of the sunscreen agent in these formulations was quantified by spectrophotometric assay of the residual sunscreen agent after irradiation for two hours using a solar simulator. The exact operating procedure was as follows:

(i) the formulae thus prepared were spread at 2 mg/cm$^2$ onto a ground polymethyl methacrylate substrate;

(ii) the samples were subsequently, subjected for two hours at constant temperature to the radiation of a HERAEUS Suntest (source: 1.8 kW long xenon arc), such as to simulate natural UV irradiation (UV-A+UV-B);

(iii) after exposure, each sample were immersed in 55 ml of methanol to extract the sunscreen agent therefrom;

(iv) the solutions thus obtained were analyzed by UV spectrophotometry in the range 290–400 nm.

The proportion of sunscreen agent which remained after irradiation is expressed mathematically by the ratio between the concentration of sunscreen agent measured in the irradiated sample and the initial concentration of this agent in the sample before irradiation.

The results obtained are reported in the following Table II:

TABLE II

| | Residual PARSOL 1789 (% of initial quantity) |
|---|---|
| F0 (Comparative) | 8% |
| F1 (Invention) | 52% |
| F2 (Invention) | 74% |

These results clearly demonstrate the marked photostabilization provided by the two amide compounds in accordance with the invention to 4-(tert-butyl)-4'-methoxydibenzoylmethane. In the comparative formula F0, the loss of sunscreen agent was 92%; it was no greater than 48% for the formula F1 and was only 26% for the formula F2.

EXAMPLE 2

In this example, the light stability of 4-(tert-butyl)-4'-methoxydibenzoylmethane (sunscreen agent "PARSOL 1789" marketed by GIVAUDAN) was investigated in the presence of various amounts of amide compound in accordance with the invention, namely ethyl N-butyl, N-acetylaminopropionate (Compound 2). In order to obtain good solubilization of the sunscreen agent at the low concentrations of amide compound, FINSOLV TN marketed by FINETEX ($C_{12}$–$C_{15}$ alkyl benzoates) was used as an additional, neutral solvent.

The compositions of the formulae which were investigated (% by weight relative to the total weight of the formulation, the common vehicle being the same as that employed in Example 1) and the degree of light stability attained (according to the same procedure as that of Example 1) are reported in Table III below:

TABLE III

| | Composition (% by weight) | | | | Residual |
|---|---|---|---|---|---|
| | PARSOL 1789 (Sunscreen agent) | COMPOUND 2 (amide) | FINSOLV TN (solvent) | COMMON VEHICLE | PARSOL 1789 |
| F0 (Comparative) | 2% | 0% | 10% | qs 100% | 8% |
| FI (Invention) | 2% | 2% | 8% | qs 100% | 16% |
| FII (Invention) | 2% | 4% | 6% | qs 100% | 24% |
| FIII (Invention) | 2% | 6% | 4% | qs 100% | 41% |
| FIV (Invention) | 2% | 8% | 2% | qs 100% | 58% |
| F2 (Invention) | 2% | 10% | 0% | qs 100% | 74% |

While the invention has been described in terms of various preferred embodiments, the skilled artisan will appreciate that various modifications, substitutions, omissions, and changes may be made without departing from the spirit thereof. Accordingly, it is intended that the scope of the present invention be limited solely by the scope of the following claims, including equivalents thereof.

What is claimed is:

1. A topically applicable, photostable sunscreen/cosmetic composition adopted for the photoprotection of human skin and/or hair, comprising an effective photoprotecting amount of at least one dibenzoylmethane compound and an effective amount of at least one amido compound photostabilizer therefor, in a cosmetically acceptable vehicle, diluent or carrier.

2. The photostable sunscreen/cosmetic composition as defined by claim 1, said at least one dibenzoyldimethane compound comprising 2-methyldibenzoylmethane, 4-methyldibenzoylmethane, 4-isopropyldibenzoylmethane, 4-tert-butyldibenzoylmethane, 2,4-dimethyldibenzoylmethane, 2,5-dimethyldibenzoylmethane, 4,4'-diisopropyldibenzoylmethane, 4-tert-butyl-4'-methoxydibenzoylmethane, 2-methyl-5-isopropyl-4'-methoxydibenzoylmethane, 2-methyl-5-tert-butyl-4'-methoxydibenzoylmethane, 2,4-dimethyl-4'-methoxydibenzoylmethane or 2,6-dimethyl-4-tert-butyl-4'-methoxydibenzoylmethane.

3. The photostable sunscreen/cosmetic composition as defined by claim 2, said at least one dibenzoylmethane compound comprising 4-(tert-butyl)-4'-methoxydibenzoylmethane or 4-isopropyldibenzoylmethane.

4. The photostable sunscreen/cosmetic composition as defined by claim 3, said at least one dibenzoylmethane compound comprising 4-(tert-butyl)-4'-methoxydibenzoylmethane.

5. The photostable sunscreen/cosmetic composition as defined by claim 1, said at least one amido compound having the following structural formula (1):

in which $R^1$, $R^2$ and $R^3$, which may be identical or different, are each a hydrogen atom or a monovalent, saturated or unsaturated, aliphatic or cycloaliphatic or cyclic hydrocarbon radical, optionally comprising at least one other group, and having from 1 to 30 carbon atoms, with the proviso that $R^1$ may together form, either with $R^2$ or with $R^3$, a ring member having from 5 to 18 carbon atoms, and that $R^2$ and $R^3$ may together form a ring member having from 5 to 18 carbon atoms.

6. The photostable sunscreen/cosmetic composition as defined by claim 5, wherein formula (1) at least one of the radicals $R^2$ and $R^3$ is other than a hydrogen atom.

7. The photostable sunscreen/cosmetic composition as defined by claim 6, wherein formula (1), both of the radicals $R^2$ and $R^3$ are other than hydrogen atoms.

8. The photostable sunscreen/cosmetic composition as defined by claim 5, wherein formula (1), at least one of $R^1$, $R^2$ and $R^3$ is a monovalent hydrocarbon radical having from 1 to 22 carbon atoms.

9. The photostable sunscreen/cosmetic composition as defined by claim 5, wherein formula (1), the radical $R^1$ is a $C_1$–$C_{12}$ linear or branched alkyl radical, or a phenyl radical optionally substituted by one or more $C_1$–$C_{12}$ linear or branched alkyl radicals.

10. The photostable sunscreen/cosmetic composition as defined by claim 5, wherein formula (1), the radical $R^2$ is a $C_1$–$C_{12}$ linear or branched alkyl radical.

11. The photostable sunscreen/cosmetic composition as defined by claim 5, wherein formula (1), $R^3$ is a linear or branched alkyl radical, or a monovalent radical containing an ester functional group and having the following structural formula (2):

in which R and R', which may be identical or different, are each a hydrocarbon radical having from 1 to 12 carbon atoms.

12. The photostable sunscreen/cosmetic composition as defined by claim 11, wherein formula (2), the radicals R and R' are hydrocarbon radicals having from 1 to 8 carbon atoms.

13. The photostable sunscreen/cosmetic composition as defined by claim 12, said hydrocarbon radicals being alkyl radicals.

14. The photostable sunscreen/cosmetic composition as defined by claim 1, said at least one amido compound comprising an N,N-diethyl-methylbenzamide having the structural formula (3):

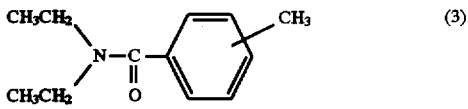

15. The photostable sunscreen/cosmetic composition as defined by claim 14, said N,N-diethyl-methylbenzamide comprising N,N-diethyl-3-ethylbenzamide.

16. The photostable sunscreen/cosmetic composition as defined by claim 1, said at least one amido compound comprising ethyl N-butyl, N-acetylaminopropionate.

17. The photostable sunscreen/cosmetic composition as defined by claim 1, comprising at least one N,N-disubstituted amido compound.

18. The photostable sunscreen/cosmetic composition as defined by claim 1, comprising at least one nonemulsifying amido compound.

19. The photostable sunscreen/cosmetic composition as defined by claim 1, comprising at least one N,N-disubstituted nonemulsifying amido compound.

20. The photostable sunscreen/cosmetic composition as defined by claim 1, comprising at least one nonionic amido compound.

21. The photostable sunscreen/cosmetic composition as defined by claim 1, comprising at least one water-insoluble amido compound.

22. The photostable sunscreen/cosmetic composition as defined by claim 1, comprising at least one nonionic, non-emulsifying and water-insoluble amido compound.

23. The photostable sunscreen/cosmetic composition as defined by claim 1, comprising from 0.01% to 10% by weight of said at least one dibenzoylmethane compound relative to the total weight thereof.

24. The photostable sunscreen/cosmetic composition as defined by claim 23, comprising from 0.01% to 50% by weight of said at least one amido compound relative to the total weight thereof.

25. A photostable sunscreen/cosmetic composition as defined by claim 1, comprising an oil-in-water or water-in-oil emulsion.

26. A photostable sunscreen/cosmetic composition as defined by claim 1, further comprising a UV-B sunscreen.

27. A photostable sunscreen/cosmetic composition as defined by claim 1, further comprising at least one cosmetically acceptable adjuvant or additive.

28. The photostable sunscreen/cosmetic composition as defined by claim 27, said at least one adjuvant or additive comprising a fat, organic solvent, ionic or nonionic thickening agent, demulcent, antioxidant, opacifying agent, stabilizing agent, emollient, silicone, α-hydroxy acid, antifoaming agent, hydrating agent, vitamin, fragrance, preservative, surfactant, filler, sequestering agent, polymer, propellant, insect repellent, basifying or acidifying agent, dye, colorant, or mixture thereof.

29. The photostable sunscreen/cosmetic composition as defined by claim 1, comprising a nonionic vesicle dispersion, cream, milk, gel, cream gel, lotion, ointment, suspension, dispersion, powder, solid stick, foam or spray.

30. The photostable sunscreen/cosmetic composition as defined by claim 1, comprising a makeup.

31. The photostable sunscreen/cosmetic composition as defined by claim 30, comprising an anhydrous or aqueous solid or paste, emulsion, suspension or dispersion.

32. The photostable sunscreen/cosmetic composition as defined by claim 1, comprising a shampoo, hair lacquer, or rinse.

33. A method for protecting human skin and/or hair against the deleterious effects of ultraviolet irradiation, comprising topically applying thereto an effective amount of the photostable sunscreen/cosmetic composition as defined by claim 1.

34. A method for protecting human skin and/or hair against the deleterious effects of solar radiation, comprising topically applying thereto an effective amount of the photostable sunscreen/cosmetic composition as defined by claim 1.

* * * * *